United States Patent [19]

Yamada et al.

[11] Patent Number: 5,305,764
[45] Date of Patent: Apr. 26, 1994

[54] MEDICAL DIAGNOSTIC APPARATUS UTILIZING LINE-OF-SIGHT DETECTION

[75] Inventors: Mitsuho Yamada; Hitoshi Hongo; Kenya Uomori; Hiroshi Yoshimatsu; Keiichi Ueno, all of Kyoto; Mitsuru Fujii, Hokkaido; Shinji Murakami, Hokkaido; Norihito Nakano, Hokkaido; Jiro Miyazawa, Hokkaido; Ryo Fukatsu, Hokkaido; Naohiko Takahata, Hokkaido, all of Japan

[73] Assignee: ATR Auditory and Visual Perception Research Laboratories, Kyoto, Japan

[21] Appl. No.: 995,401

[22] Filed: Dec. 18, 1992

[30] Foreign Application Priority Data

Jul. 9, 1992 [JP] Japan .................................. 4-182226

[51] Int. Cl.$^5$ ............................................. A61B 13/00
[52] U.S. Cl. .................................................... 128/745
[58] Field of Search ................ 128/745, 782; 351/210, 351/211

[56] References Cited

U.S. PATENT DOCUMENTS

| | | | |
|---|---|---|---|
| 4,158,920 | 6/1979 | Walker | 128/745 |
| 4,838,681 | 6/1989 | Pavlidis | 128/745 |
| 4,848,340 | 7/1989 | Bille et al | 128/745 |
| 5,070,883 | 12/1991 | Kasahara | 128/745 |

FOREIGN PATENT DOCUMENTS 9117705  11/1991  World Int. Prop. O. .......... 128/782

Primary Examiner—Max Hindenburg
Attorney, Agent, or Firm—Lowe, Price, LeBlanc & Becker

[57] ABSTRACT

In the medical diagnostic apparatus employing line-of-sight detection, eye movement and head movement of a subject are detected by eye movement detecting portion and head movement detecting portion, respectively, and images of the field of view of the subject are picked up by a TV camera. A calculating portion calculates a locus of the line-of-sight, a locus of the eye movement, the locus of the head movement, and vectors of spatial movement of the line-of-sight in response to the detected eye movement and the head movement. An image processing portion reduces the picked up image, a superimposer superimposes the images of the loci, the vector images and the images of the reduced field of view on each other, and the resulting images are displayed on a CRT display.

8 Claims, 7 Drawing Sheets

MEDICAL DIAGNOSTIC APPARATUS UTILIZING LINE-OF-SIGHT DETECTION

BACKGROUND OF THE INVENTION

1. Field of the Invention

The present invention relates to a medical diagnostic apparatus utilizing line-of-sight detection, and more specifically, it relates to a medical diagnostic apparatus which enables diagnoses of diseases related to brain function such as dementia by detecting line-of-sight of a subject.

2. Description of the Background Art

The number of patients suffering from Alzheimer's disease is estimated to be four million in the United States and about a million in Japan. Compared with senile dementia such as cerebrovascular disease popular among Japanese, the cause of Alzheimer's disease is not known, and much effort has made to find the cause so as to enable early diagnosis and early medical treatment. However, it is difficult to discriminate Alzheimer's disease from cerebrovascular disease when there is no typical symptoms. There has been a strong demand of accurate method of discrimination, since development of disease, pharmaceutical treatment and so on are different for these diseases.

Hachinski's ischemic score has been proposed as a method of discriminating these two diseases. According to this ischemic score, a point is given dependent on whether or not the patient has an anamnesis of apoplexy, cerebral infraction or the like and if the points exceeds a prescribed number, it is determined as the cerebrovascular disease, and otherwise it is determined to be Alzheimer's disease. However, discrimination is still difficult by this method if the patient has no such anamnesis.

It has been known that neuropsychological symptom which is considered to be an impairment of "tool disfunction" such as visual cognitive disfunction appears from relatively early period of Alzheimer's disease. In view of this fact, Fujii et al. has reported the following analysis carried out by utilizing eye movement. More specifically, a problem of copying a cube on the right side while watching an original of the cube on the left side is presented. Even a patient who is in the initial stage I of Alzheimer's disease and does not show apparent constructional apraxia is reported to show characteristic symptom similar to a so called Balint syndrome; that is, the patient cannot stare at on point, or more specifically, abnormal distribution of gazing point appears, saccade deviated from both the presented cube and the depicted drawing by the patient is generated, or the point of gazing is fixed at the same point for a long period of time. In Alzheimer's disease, it is supposed from MRI (nuclear magnetic periorbital inspection) that there is caused disfunction of parietal lobe which is related to spatial vision. Accordingly, constructional disfunction derived from degradation in function of the rear association areas with the parietal lobe being the center, degradation of function of positional recognition of a target point or recognition of depth derived from disfunction of external spatial vision such as disfunction of eye movement, disfunction of coordinate transformation system between the coordinate of eye movement system and the coordinate of the center of one's body axis, or visual-motor disfunction, is supposed to be a possible cause of the aforementioned symptoms.

SUMMARY OF THE INVENTION

Therefore, an object of the present invention is to provide a medical diagnostic apparatus using line-of-sight detection which facilitates diagnosis of diseases related to brain function by noting movement of one's line-of-sight implemented by the eye movement or head movement of the subject, and by displaying the movement of one's line-of-sight in terms of vectors.

Briefly stated, in the present invention, head movement and eye movement of a subject are detected, and in response to the detected outputs, spatial movement of the line-of-sight of the subject is calculated, and the calculated movement of the line-of-sight is represented by vectors.

Therefore, according to the present invention, specific movement of line-of-sight particular in diseases related to brain function such as Alzheimer's disease can be easily found, which is useful in medical and crinical diagnosis and rehabilitation.

In a preferred embodiment of the present invention, locus of the line-of-sight, the locus of eye movement and the locus of head movement are calculated and displayed respectively, in accordance with the detected head movement and the eye movement.

In a more preferred embodiment of the present invention, the images of the visual field of the subject is picked up, the picked up image is reduced in size, and the reduced image is displayed combined with the images of the locus of the line-of-sight, the locus of eye movement and the locus of head movement.

Therefore, in this more preferred embodiment of the present invention, the movement of the subject who is working can be compared with the loci, which enables more definite diagnosis of the subject.

The foregoing and other objects, features, aspects and advantages of the present invention will become more apparent from the following detailed description of the present invention when taken in conjunction with the accompanying drawings.

DESCRIPTION OF THE PREFERRED EMBODIMENTS

Figure 1:
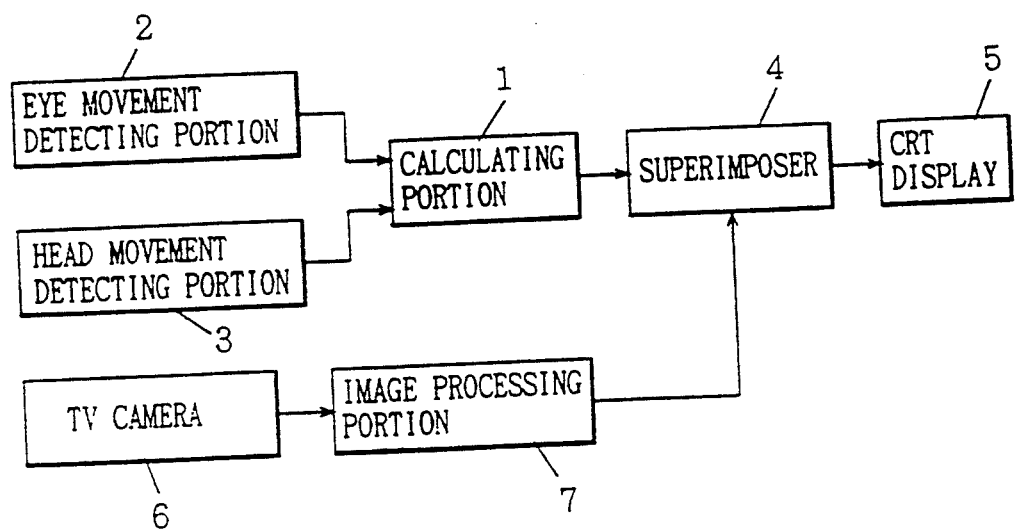
FIG. 1 is a schematic block diagram showing one embodiment of the present invention.

FIG. 1 is a schematic block diagram of one embodiment of the present invention. Referring to FIG. 1, an eye movement detecting portion 2 detects eye movement of a subject, and the detection output thereof is applied to a calculating portion 1. A head movement detecting portion 3 detects the head movement of the subject, and the detection output thereof is applied to the calculating portion 1. In response to the detection outputs from the eye movement detecting portion 2 and the head movement detecting portion 3, the calculating portion 1 calculates the vectors of spatial movement of the line-of-sight of the subject, the locus of the line-of-sight, the locus of eye movement and the locus of head movement. The images of the calculated vectors and of the loci are displayed on a CRT display 5.

In a more preferred embodiment, a TV camera 6 is provided to pick up the images of the field of view of the subject. The image output from the TV camera 6 is applied to an image processing portion 7. The image processing portion 7 includes a memory which stores the picked up image in, for example, a digital manner, and the image data stored in the memory is reduced and applied to a superimposer 4. The superimposer 4 superimposes the reduced image on the images of the vectors and of the loci calculated by the calculating portion 1, and the resulting images are displayed on the CRT display 5.

Figure 2:
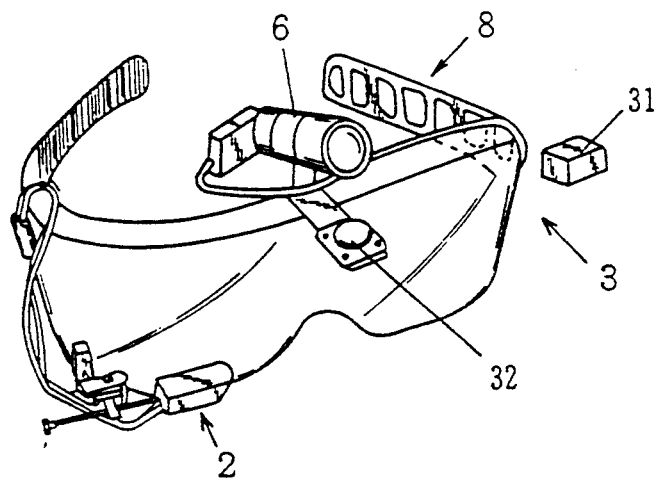
FIG. 2 is an illustration of the eye movement detecting portion, the head movement detecting portion and a TV camera shown in FIG. 1 attached to goggles.
Figure 3:
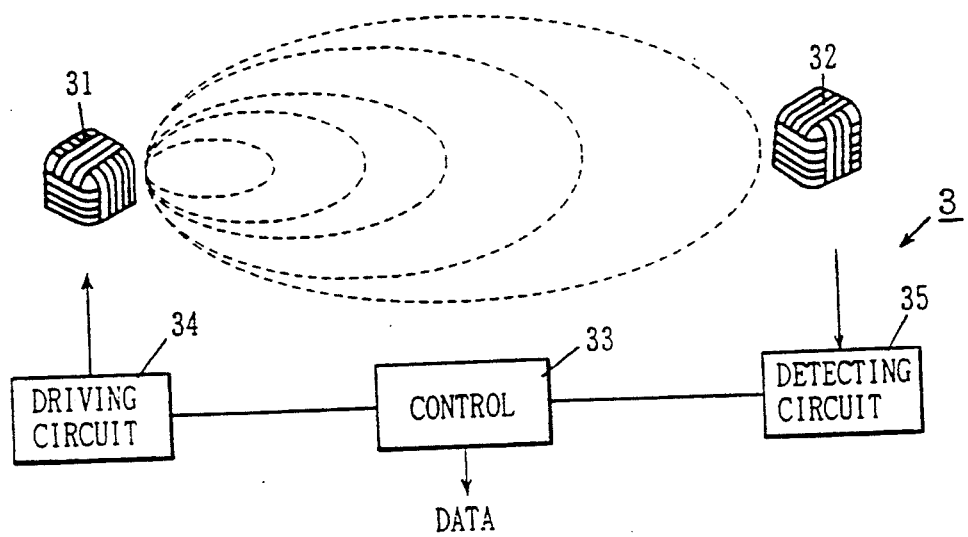
FIG. 3 shows a specific example of the head movement detecting portion.

FIG. 2 is an illustration showing the eye movement detecting portion 2, the head movement detecting portion 3 and the TV camera 6 shown in FIG. 1 attached to goggles, FIG. 3 shows a specific example of the head movement detecting portion 3, and FIG. 4 shows a specific example of the eye movement detecting portion 2.

Figure 4A:
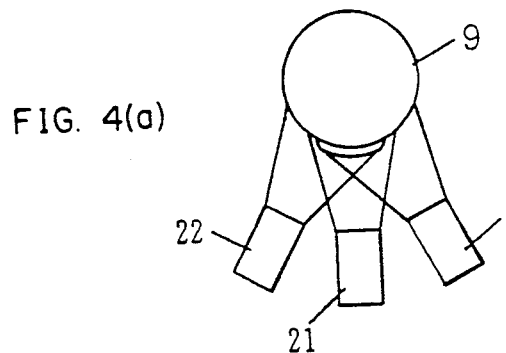
FIGS. 4(a)–(c) show a specific example of the eye movement detecting portion.
Figure 4B:
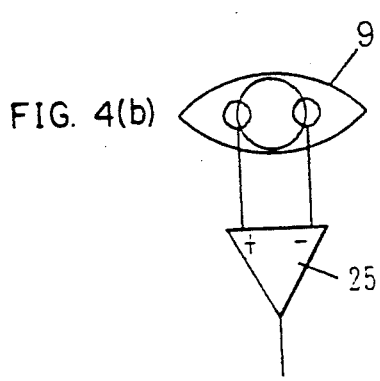
Figure 4C:
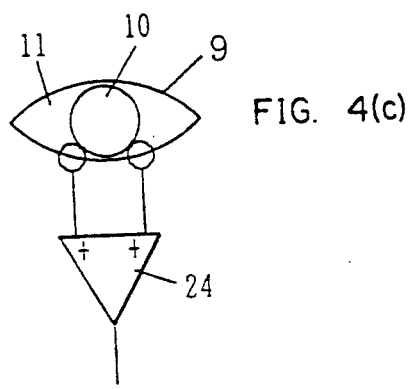

The goggles 8 shown in FIG. 2, which the subject wears, has a TV camera 6 for picking up images of the field of view of the subject attached at the upper central portion. The eye movement detecting portion 2 is attached at a lower portion of one side of the goggles 8. The eye movement detecting portion 2 includes a light emitting diode 21 provided at the center and the photodiodes 22 and 23 provided on both sides thereof as shown in FIG. 4(a). A light emitting diode radiating infrared rays having relatively wide directivity of about ±21° is used as the light emitting diode 21, while ones having acute directivity of about ±10° are used as the photodiodes 22 and 23. The light beam emitted from the light emitting diode 21 to the eye ball 9 is reflected from the iris of the eye 10 and from the white if the eye 11 with different reflectivity, and the difference in reflectivity is amplified by an operational amplifier 25. If the difference is calculated, a horizontal output (left and right) is obtained as shown in FIG. 4(b), and if the sum is calculated by an operation amplifier 24, a vertical (up and down) output is obtained as shown in FIG. 4(c).

The head movement detecting portion 3 is formed of a magnetic sensor as shown in FIG. 3. More specifically, the head movement detecting portion 3 includes a orthogonal coil serving as a source 31 and an orthogonal coil serving as a sensor 32. In accordance with an instruction from a control portion 33, a driving circuit 34 drives the orthogonal coil of the source 31 to generate a magnetic field. When the subject wearing the head movement detecting portion 3 moves, a voltage is induced in the sensor 32, which voltage is detected by the detecting circuit 35, the detected output therefrom is calculated by the control portion 33, and thus data corresponding to the movement of the head is output.

Figure 5A:
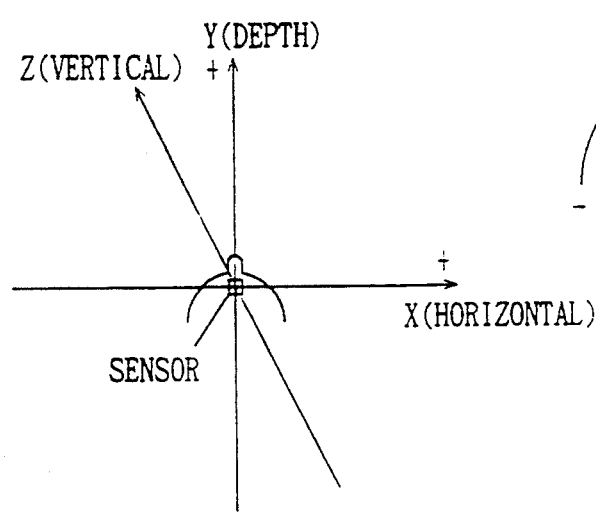
FIGS. 5(a)–(b) show the principle of the head coordinate system with the subject being the center.
Figure 5B:
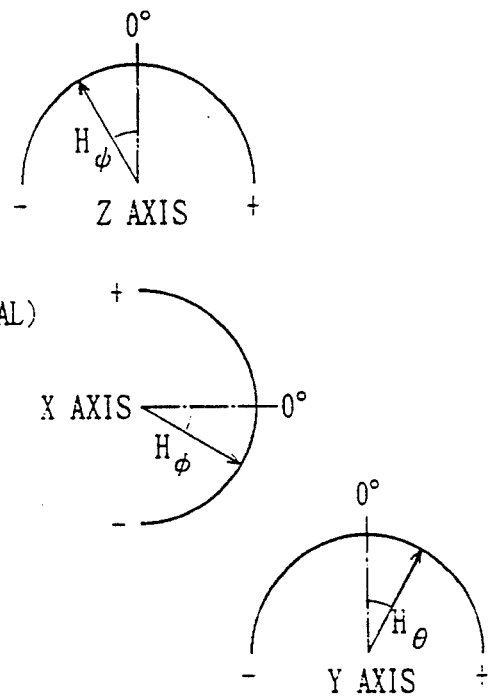

FIG. 5 is an illustration showing the principle of the head coordinate system with the subject being the center. Referring to FIG. 5, the head coordinate system detected by the head movement detecting portion 3 will be described. The head coordinate system includes two systems, that is, XY coordinate system realized by the translational movement of the subject with respect to the object of monitoring such as shown in FIG. 5(a), and a polar coordinate system based on the rotation movement of the head such as shown in FIG. 5(b). The amount of head movement in respective coordinate systems are defined as (Hx, Hy, Hz), (H$\psi$, H$\phi$, H$\theta$). In this embodiment, the direction toward the object of monitoring is represented by the Y axis, the horizontal movement is represented by the X axis and the vertical movement is represented by the Z axis, as an example. H$\phi$ represents the rotation of the X axis, that is, the movement of one's neck upward or downward. H$\theta$ represents the rotation of the Y axis, that is, the movement of inclining ones neck once from the left shoulder to the right shoulder. H$\psi$ represents rotation in the Z axis, that is, rotation of one's neck in the left or right direction.

The line-of-sight changes by the horizontal movement of the head (Hx, Hy, Hz), and when this movement is changed in the equivalent of rotation angle of the eye ball (Ex, Ey), the following equations are obtained.

$$Ex = 180/\pi \cdot \tan^{-1} Hx / (D+Hy) \qquad (1)$$

$$Ey = 180/\pi \cdot \tan^{-1} Hz / (D+HY) \qquad (2)$$

where D: distance from the subject to the point of gazing.

When the neck is inclined by H$\theta$ to the left shoulder or to the right shoulder, the coordinate of the eye movement system rotates. Therefore, the eye movement coordinate system (Xe, Ye) inclined by H$\theta$ must be changed to the coordinate system (Xe', Ye') which is orthogonal to the original object of monitoring.

$$Xe' = Xe \cdot \cos H\theta + Ye \cdot \sin H\theta \qquad (3)$$

$$Ye' = -Xe \cdot \sin H\theta + Ye \cdot \cos H\theta \qquad (4)$$

The movement of the line-of-sight (Xh, Yh) realized by the head movement is represented by the following equations (5) and (6) derived from the equations (1) and (2).

$$Xh = Ex + H\psi \qquad (5)$$

$$Yh = Ey + H\phi \qquad (6)$$

Therefore, the movement of the line-of-sight (Vx, Vy) taking the head movement into account is represented by the following equations (7) and (8), from equations (3) to (6).

$$Vx = Xe' + Xh \qquad (7)$$

$$Vy = Ye' + Yh \qquad (8)$$

By employing the equations (7) and (8) above, the ordinary movement of one's line-of-sight effected by combining head movement and eye movement can be reproduced.

Figure 6:
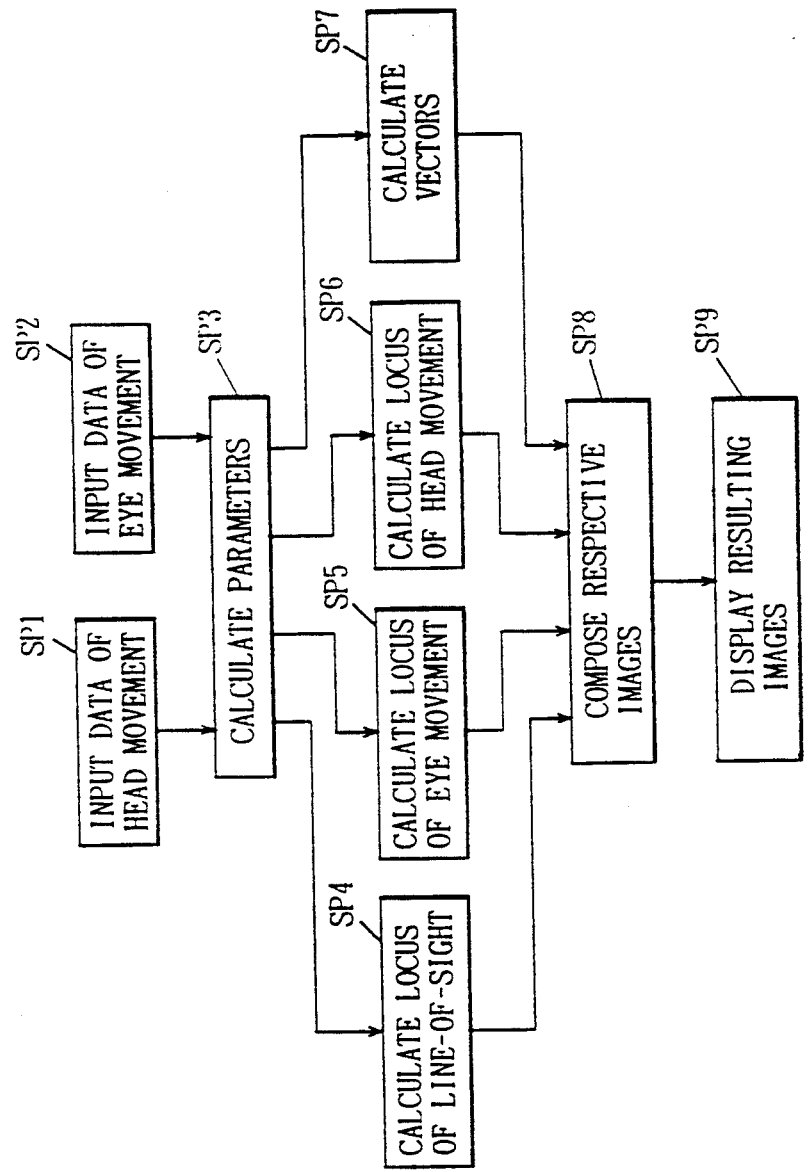
FIG. 6 is a flow chart showing specific operation of one embodiment of the present invention.

FIG. 6 is a flow chart showing a specific operation of one embodiment of the present invention, and FIG. 7 shows an example of display in accordance with one embodiment of the present invention.

The specific operation of one embodiment of the present invention will be described with reference to FIGS. 1 to 7. In step SP1 (simply referred to as SP in the drawings), the amount of head movement (Hx, Hy, Hz), (H$\psi$, H$\phi$, H$\theta$) described with respect to FIG. 5 is applied as the data of head movement from the head movement detecting portion 3 to the calculating portion 1. In step SP2, the eye ball coordinate system (Xe, Ye) is applied as the data of eye movement from the eye movement detecting portion 2 to the calculating portion 1. In step SP3, the calculating portion 1 carries out calculations of the above mentioned equations (1) to (8) in each of the sampling periods i, i+1, i+2 . . . Consequently, the values of H$\psi_i$, H$\phi_i$, H$\theta_i$, Hx$_i$, Hy$_i$, Hz$_i$, X'e$_i$, Y'e$_i$, Vx$_i$ and Vy$_i$ of each sampling period are calculated. In step SP4, the calculating portion 1 calculates the locus of the line-of-sight. More specifically, the calculating portion 1 connects the lien of sight (Vx$_i$, Vy$_i$) with (Vx$_{i+1}$, Vy$_{i+1}$) by a locus. In step SP5, the calculating portion 1 calculates the locus of the eye movement. More specifically, a locus between the eye movements (Xe$_i$, Ye$_i$) and (Xe$_{i+1}$, Ye$_{i+1}$) is connected. Further, the calculating portion 1 calculates the locus of the head movement in step SP6. Namely, the calculating portion 1 provides a locus connecting the head movements (H$\psi_i$+Hx$_{i+1}$, X$\phi_i$+Hy$_i$) and (H$\psi_{i+1}$, +Hx$_i$, H$\phi_{i+1}$+Hy$_{i+1}$). Further, the calculating portion 1 calculates the vectors in step SP7. Namely, the calculating portion 1 calculates the vectors of respective parameters, that is ($\downarrow$Xe$_i$, $\downarrow$Ye$_i$), ($\downarrow$H$\psi_i$, $\downarrow$H$\phi_i$), ($\downarrow$Hx$_i$, $\downarrow$Hy$_i$), and ($\downarrow$Vx$_i$, $\downarrow$Vy$_i$), (where $\downarrow$ represents a vector). In step SP8, the calculating portion 1 forms images of the loci and vectors calculated in the steps SP4–SP7, and the images are displayed on the CRT display 5 in step SP9. The resulting display is as shown in FIG. 7.

Figure 7C:
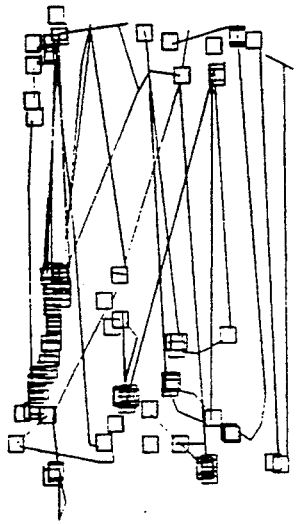
FIGS. 7(a)–(d) show an example of display in accordance with one embodiment of the present invention.
Figure 7D:
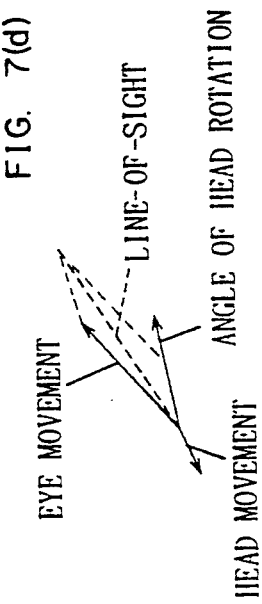
Figure 7A:
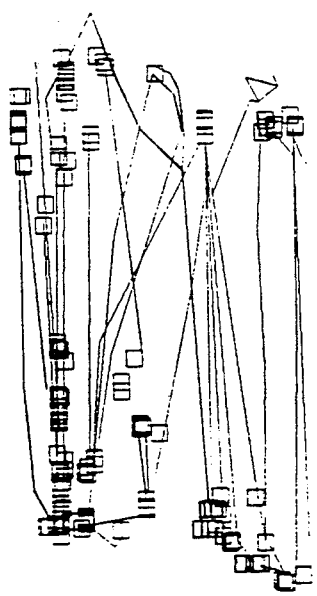
Figure 7B:

More specifically, the screen of the CRT display 5 is divided into four. In the displaying area of FIG. 7(a), the locus of the line-of-sight (Vx, Vy) of the subject during working calculated in step SP4 is displayed. In the displaying area of FIG. 7(b), the locus of the head movement (H$\psi$+Ex, H$\phi$+Ey) calculated in step SP6 is displayed. In the displaying area of FIG. 7(c), the locus of the eye movement (Xe, Ye) calculated in step SP5 is displayed. In the displaying area of FIG. 7(d), vectors of respective components (Xe, H$\psi$, Ex, Ye, H$\phi$, Ey) of the line-of-sight calculated in step SP7 are displayed. The resultant vector (Vx, Vy) is displayed in different colors dependent on the amount of eye movement, the angle of rotation of the head and the angle of transnational movement of the head occupying the magnitude thereof, so that the share of respective components, or the head share, i.e. ratio of head movement can be recognized at one sight. In the example of display shown in FIG. 7, the head movement during working is extremely reduced as compared with a healthy person as shown in FIG. 7(b), and accordingly the characteristics of Alzheimer's disease can be immediately grasped by the doctor or by the inspector.

Figure 8:
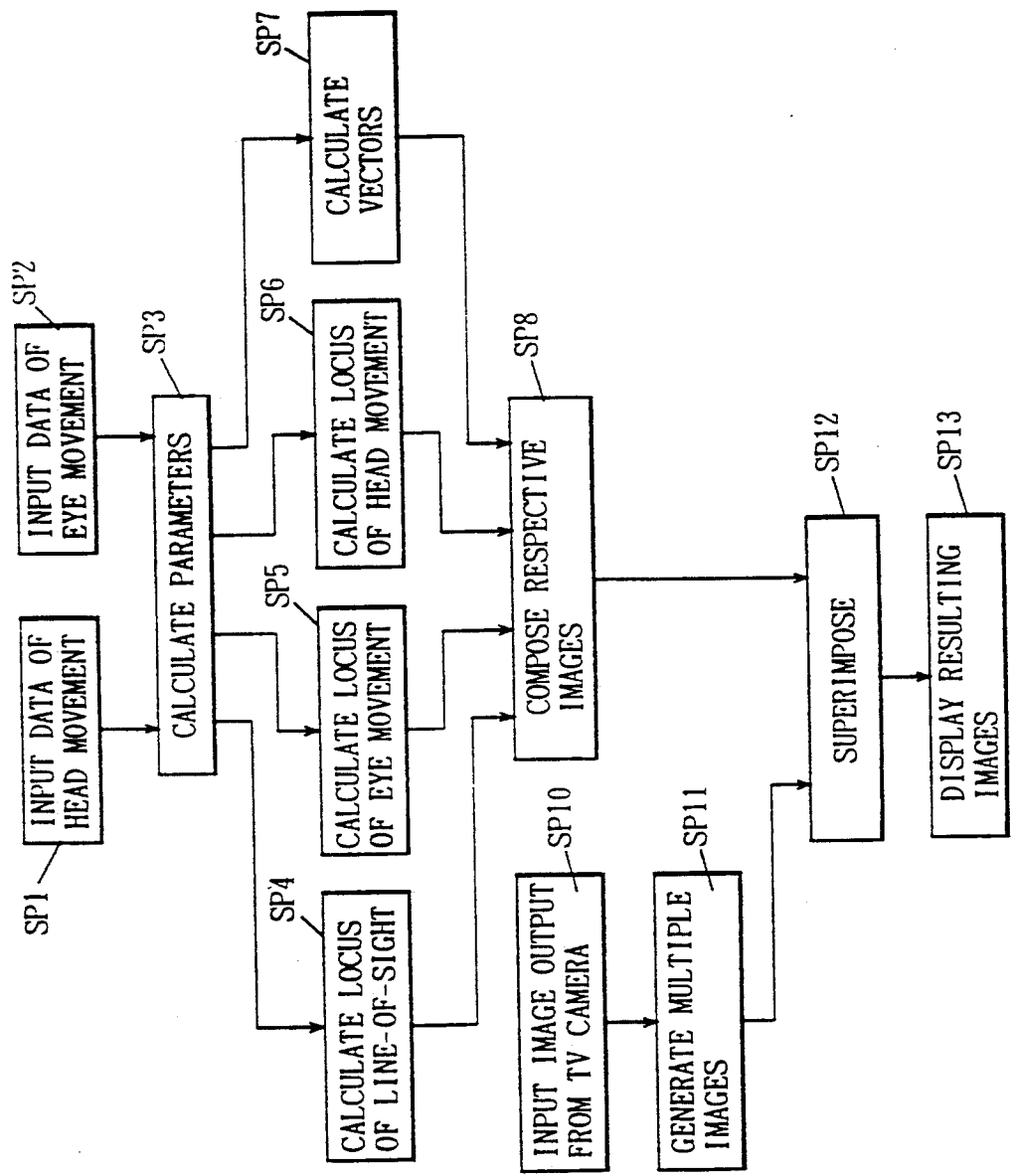
FIG. 8 is a flow chart showing a more preferred embodiment of the present invention.

FIG. 8 is a flow chart showing a more preferred embodiment of the present invention, and FIG. 9 shows an example of display.

In the embodiment shown in FIG. 8, the steps SP1–SP8 are the same as those shown in FIG. 6. In step SP10, an image signal output from a TV camera 6 shown in FIG. 1 is applied to the image processing portion 7. In step SP11, the image processing portion 7 stores the image signal output from the TV camera 6 in a digital memory, reduces the same and generates three identical images. The image signals are applied to the superimposer 4 in step SP12, superimposed on the image formed in step SP8, and the resulting image is displayed on the CRT display 5 in step SP13.

Figure 9C:
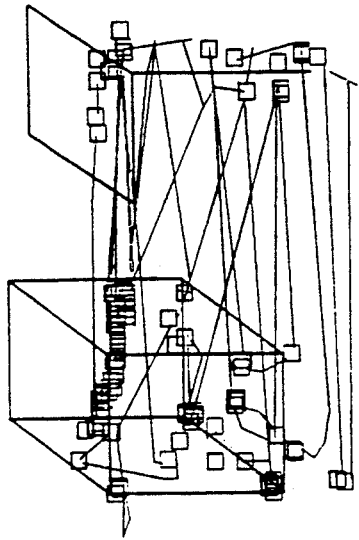
FIGS. 9(a)–(d) show a sample of display of the more preferred embodiment of the present invention.
Figure 9D:
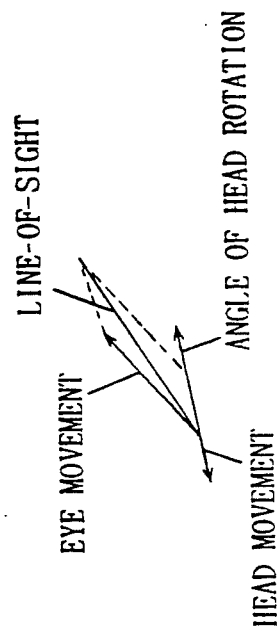
Figure 9A:
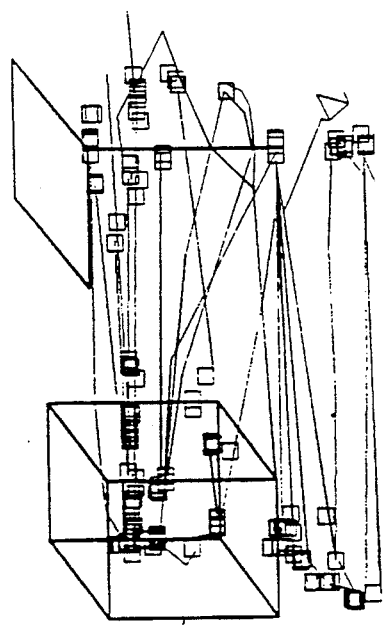
Figure 9B:
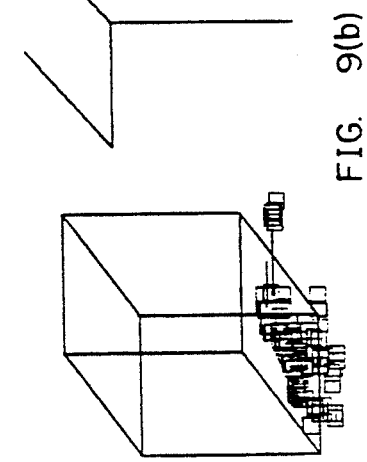

As a result, the image of the field of view while the subject is copying the cube on the right side while looking at the original of the cube on the left side and the locus of the line-of-sight during the work (Vx, Vy) are displayed combined with each other as shown in FIG. 9(a). The image of the field of view of the subject and the locus of the head movement (H$\psi$+Ex, H$\phi$+Ey) are displayed combined with each other as shown in FIG. 9(b), and the image of the field of view of the subject and the locus of the eye movement (Xe, Ye) are displayed combined with each other as shown in FIG. 9(c).

In this embodiment, the image of the field of view of the subject is displayed overlapped with the loci heretofore, and therefore, the movement of the subject during working and the loci can be monitored in correspondence, which enables more definite diagnosis on the subject.

Although the locus of the line-of-sight (Vx, Vy) during working, the locus of the head movement (H$\psi$+Ex, H$\phi$+Ey), the locus of the eye movement (Xe, Ye) and the vector components are displayed on the divided screen of the CRT display 5 in the above described embodiments, it is not limited thereto and each locus or vector may be displayed by itself.

As described above, according to the embodiments of the present invention, head movement and eye movement of a subject are detected, the spatial movement of the line-of-sight of the subject is calculated corresponding to the detected outputs, and the calculated movement of the line-of-sight is displayed in terms of vectors. Therefore, diseases related to brain function such as Alzheimer's disease can be exactly discriminated from disfunctions or diseases popular among those advanced in age, and the present invention is promising in the field of crinical diagnosis and rehabilitation.

Although the present invention has been described and illustrated in detail, it is clearly understood that the same is by way of illustration and example only and is not to be taken by way of limitation, the spirit and scope of the present invention being limited only by the terms of the appended claims.

We claim:

1. A medical diagnostic apparatus employing line-of-sight detection for diagnosing diseases related to brain function by detecting the line-of-sight of a subject, comprising:

head movement detecting means for detecting head movement of said subject;

eye movement detecting means for detecting eye movement of said subject;

calculating means responsive to an output from said head movement detecting means and to an output from said eye movement detecting means for calculating spatial movement of the line-of-sight of said subject; and displaying means for displaying the movement of the line-of-sight calculated by said calculating means in terms of vectors thereby enabling diseases related to brain function to be detected.

2. The medical diagnostic apparatus employing line-of-sight detection according to claim 1, wherein said calculating means includes means responsive to the output from said head movement detecting means and to the output from said eye movement detecting means for calculating a locus of the line-of-sight to be displayed on said displaying means.

3. The medical diagnostic apparatus employing line-of-sight detection according to claim 2, further comprising:
   image pick-up means for picking up an image in a field of view of said subject; and
   image processing means for reducing the image picked up by said image pick-up means, combining the reduced image with images calculated by said calculating means to be displayed on said displaying means.

4. The medical diagnostic apparatus employing line-of-sight detection according to claim 1, wherein
   said calculating means includes means responsive to the output from said head movement detecting means and the output from said eye movement detecting means for calculating a locus of the eye movement to be displayed on said displaying means.

5. The medical diagnostic apparatus employing line-of-sight detection according to claim 4, further comprising:
   image pick-up means for picking up an image in a field of view of said subject; and
   image processing means for reducing the image picked up by said image pick-up means, combining the reduced image with images calculated by said calculating means to be displayed on said displaying means.

6. The medical diagnostic apparatus employing line-of-sight detection according to claim 1, wherein
   said calculating means includes means responsive to the output from said head movement detecting means for calculating a locus of the head movement to be displayed on said displaying means.

7. The medical diagnostic apparatus employing line-of-sight detection according to claim 6, further comprising:
   image pick-up means for picking up an image in a field of view of said subject; and
   image processing means for reducing the image picked up by said image pick-up means, combining the reduced image with images calculated by said calculating means to be displayed on said displaying means.

8. The medical diagnostic apparatus employing line-of-sight detection according to claim 1 further comprising:
   image pick-up means for picking up an image in a field of view of said subject; and
   image processing means for reducing the image picked up by said image pick-up means, combining the reduced image with images calculated by said calculating means to be displayed on said displaying means.

* * * * *